(12) United States Patent
Just et al.

(10) Patent No.: US 8,058,329 B2
(45) Date of Patent: Nov. 15, 2011

(54) NITROUS BRIDGED DERIVATIVES OF 6H-DIBENZ[C,E][1,2]-OXAPHOSPHORINE-6-OXIDES, PROCESS FOR THE PREPARATION AND USE THEREOF

(75) Inventors: Berthold Just, Hamburg (DE); Uwe Dittrich, Radebeul (DE); Holger Keller, Sindelfingen-Darmsheim (DE); Manfred Doering, Woerth-Büchelberg (DE); Uwe Storzer, Karlsruhe (DE); Michael Ciesielski, Merseburg (DE)

(73) Assignee: Schill+Seilacher "Struktol" Aktiengesellschaft (DE)

( * ) Notice: Subject to any disclaimer, the term of this patent is extended or adjusted under 35 U.S.C. 154(b) by 901 days.

(21) Appl. No.: 10/598,012
(22) PCT Filed: Nov. 3, 2005
(86) PCT No.: PCT/EP2005/011785
 § 371 (c)(1),
 (2), (4) Date: Aug. 15, 2006
(87) PCT Pub. No.: WO2006/084488
 PCT Pub. Date: Aug. 17, 2006

(65) Prior Publication Data
 US 2008/0167405 A1 Jul. 10, 2008

(30) Foreign Application Priority Data
 Feb. 9, 2005 (DE) .......................... 10 2005 005 879

(51) Int. Cl.
 C04B 24/26 (2006.01)
 C08K 3/00 (2006.01)
 C04B 28/04 (2006.01)
 C07D 251/00 (2006.01)
 C07F 9/02 (2006.01)

(52) U.S. Cl. ................... 524/5; 524/6; 524/8; 544/214; 558/76

(58) Field of Classification Search .................. 524/5, 6, 524/8; 544/214; 558/76
 See application file for complete search history.

(56) References Cited

U.S. PATENT DOCUMENTS
4,086,206 A * 4/1978 Saito et al. .................... 524/100
(Continued)

FOREIGN PATENT DOCUMENTS
DE 2034887 1/1972
(Continued)

OTHER PUBLICATIONS
Toshio Koizumi, "Pd(0) catalyzed polyaddition of bifunctional vinyloxiranes with 1, 3-dicarbonyl compounds" Journal of Polymer Science: Part A: Polymer Chemistry, vol. 40, 2002, pp. 2487-2494.
(Continued)

*Primary Examiner* — James O Wilson
*Assistant Examiner* — Ebenezer O. Sackey
(74) *Attorney, Agent, or Firm* — Hayes Soloway P.C.

(57) ABSTRACT

Nitrous bridged derivatives of 6H-dibenz[c,e][1,2]-oxaphosphorine-6-oxides, process for the preparation and use thereof.

The invention refers to nitrous bridged derivatives of 6H-dibenz[c,e][1,2]-oxaphosphorine-6-oxides, a process for the preparation thereof and their use as flameproofing agents for polymers such as polyesters, polyamides, polycarbonates, polystyrenes, polyethylene, polypropylene, phenolic and epoxy resins. The derivatives have the Formulae I or II:

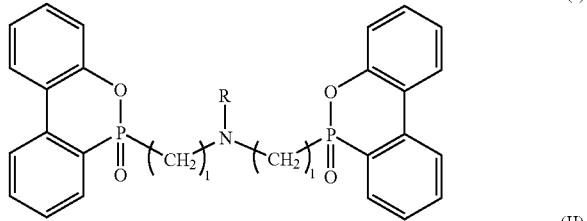

(I)

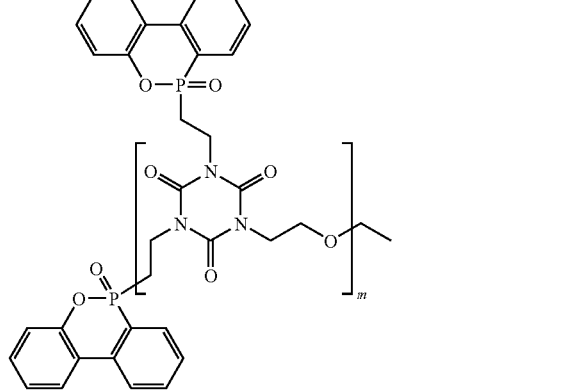

(II)

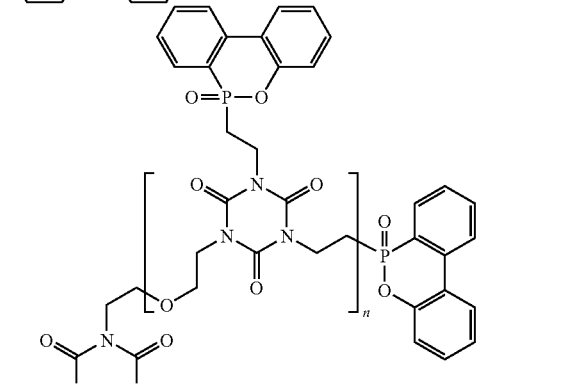

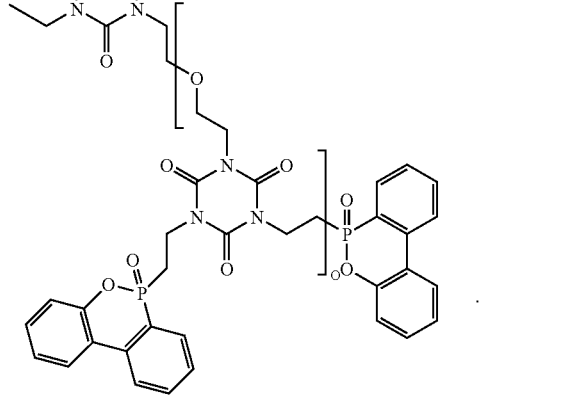

23 Claims, No Drawings

U.S. PATENT DOCUMENTS

| | | | | |
|---|---|---|---|---|
| 4,127,590 | A | 11/1978 | Endo et al. | 260/346.74 |
| 4,529,533 | A | 7/1985 | Chasar | 524/101 |
| 4,742,088 | A | 5/1988 | Kim | 521/118 |
| 5,821,376 | A | 10/1998 | Rathfelder et al. | 558/82 |
| 6,797,821 | B2 | 9/2004 | Wang et al. | 544/195 |
| 7,115,765 | B2 | 10/2006 | Sprenger et al. | 558/82 |
| 2005/0038279 | A1 | 2/2005 | Dittrich et al. | 558/97 |

FOREIGN PATENT DOCUMENTS

| | | |
|---|---|---|
| DE | 26 46 218 | 4/1977 |
| DE | 2646218 | 4/1977 |
| DE | 19522876 | 11/1996 |
| DE | 10206982 | 9/2003 |
| DE | 10359269 | 7/2005 |
| EP | 0 806 429 | 11/1977 |
| EP | 0 106 169 | 4/1984 |
| JP | 61-162541 * | 7/1986 |
| JP | 2001-172555 | 6/2001 |
| JP | 2001-323268 * | 11/2001 |
| JP | 2001 354685 | 12/2001 |
| JP | 2002-284850 | 10/2002 |
| JP | 2003-105058 | 4/2003 |
| WO | WO 02/14334 | 2/2002 |
| WO | WO 2004/024791 | 3/2004 |

OTHER PUBLICATIONS

International Preliminary Report on Patentability, PCT/Written Opinion of ISR Authority.

Liu, et al., "Phosphorus-Containing Epoxy for Flame Retardant. III: Using Phosphorylated IDiamines as Curing Agents", Phosphorylated Diamines as Curing Agents, pp. 895-901, May 22, 1996.

Liu, et al., "Synthesis, Characterization, Thermal, and Flame Retardant Properties of Phosphate-Based Epoxy Resins", Phosphate-Based Epoxy Resins, pp. 565-574, Jul. 16, 1996.

Levchik, et al., "Thermal Decomposition of Cyclotriphosphazenes. I. Alkyl-Aminoaryl Ethers", Thermal Decomposition of Ctps. I, pp. 461-472, Jun. 10, 1997.

Lu, et al., "Recent developments in the chemistry of halogen-free flame retardant polymers", Prog. Polym. Sci. 27 (2002) pp. 1661-1712, Mar. 6, 2002.

Levchik et al., "Epoxy resins cured with aminophenylmethylphosphine oxide-II. Mechanism of thermal decomposition", Polymer Degradation and Stability 60 (1998), pp. 169-183, Jan. 20, 1997.

Wang et al., Synthesis and Properties of Epoxy Resins Containing 2-(6-oxid-6H-dibenz(c,e)(1,2) oxaphosphorin-6-yl) 1,4-benzenediol (II), Polymer 41, 3631-3638, 2000.

Shieh et al., "Effect of the Organophosphate Structure on the Physical and Flame-Retardant Properties of an Epoxy Resin", Journal of Polymer Science: Part A: Polymer Chemistry, vol. 40, 369-378, 202.

PCT International Search Report and Written Opinion, dated Mar. 7, 2006.

* cited by examiner

NITROUS BRIDGED DERIVATIVES OF 6H-DIBENZ[C,E][1,2]-OXAPHOSPHORINE-6-OXIDES, PROCESS FOR THE PREPARATION AND USE THEREOF

The invention relates to nitrous bridged derivatives of 6H-dibenz[c,e][1,2]-oxaphosphorine-6-oxides, a process for preparation thereof, their use as flameproofing agents for polymers, and products prepared therefrom.

Dibenz[c,e][1,2]-oxaphosphorine-6-oxide, also called "DOPO", and derivatives thereof have been known for a long time as effective flameproofing agents for polymers (DT2034887 C3, DT 2646218 A1, DE 19522876 C1).

Amino derivatives of aryl phosphanoxides (J. Appl. Polym. Sci. 1997, 63, 895), phosphoric acid aryl esters (J. Polym. Sci. A: Polym. Chem. 1997, 35, 565) and phosphazenes (J. Appl. Polym. Sci. 1998, 67, page 461; Progr. Polym. Sci. 2002, 27, page 1680) are known from the literature as reactive flameproofing agents (Polymer Degr. Stab. 1998, 60, 160).

Due to the demonstrated flameproofing effect of dibenz[c,e][1,2]-oxaphosphorine-6-oxides, there have been tested amino derivatives of said compounds, for example, a series of different 6-aminomethyl-derivatives (JP 2003-105058, JP 2002-284850, U.S. Pat. No. 4,742,088) all of which have been produced by amino methylation of 6H-dibenz[c,e][1,2]-oxaphosphorine-6-oxide with formaldehyde and primary or secondary amines. A disadvantage of such 6-aminomethyl derivatives is that in the presence of water, a back reaction to educts develops with release of the 6H-dibenz[c,e][1,2]-oxaphosphorine-6-oxides. In fact, the back reaction is favored at elevated temperatures used in the integration of flameproofing agents into thermoplastic polymers. However, the undesired release of 6H-dibenz[c,e][1,2]-oxaphosphorine-6-oxides in turn results in acid decomposition of many thermoplastic polymers.

However, there have not heretofore been described nitrous bridged derivatives of 6H-dibenz[c,e][1,2]-oxaphosphorine-6-oxides which have more than one bridge carbon atom between the phosphorus atom of the phosphaoxaphenanthrene annular system and the nitrogen atom of the bridge. Nor have polymeric nitrous bridged derivatives of 6H-dibenz[c,e][1,2]-oxaphosphorine-6-oxides heretofore been described.

An object of this invention is to provide nitrous bridged derivatives of 6H-dibenz[c,e][1,2]-oxaphosphorine-6-oxides, a process for the preparation thereof, and a process for the use thereof. A more particular object of the invention is to provide a process which overcomes the above mentioned disadvantages of the prior art, and more particularly, to provide a process that starts from commercially easily obtainable DOPO or derivatives thereof, a process that is as simple and cheap as possible and provides a route of synthesis which is as halogen-free as possible.

According to the invention the aforesaid problems are solved by the processes for the preparation of the compounds according to claims 1 to 13, the compounds of claims 14 to 17, with said compounds having the Formulae I and II, as well as the use thereof as flameproofing agents for polymers and products made thereof. Preferred embodiments result from the dependant claims.

The present invention provides a process for preparing nitrous bridged derivatives of 6H-dibenz[c,e][1,2]-oxaphosphorine-6-oxides of the Formulae (I) and (II)

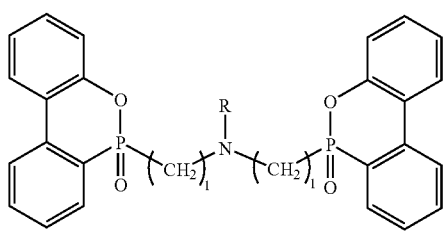

(I)

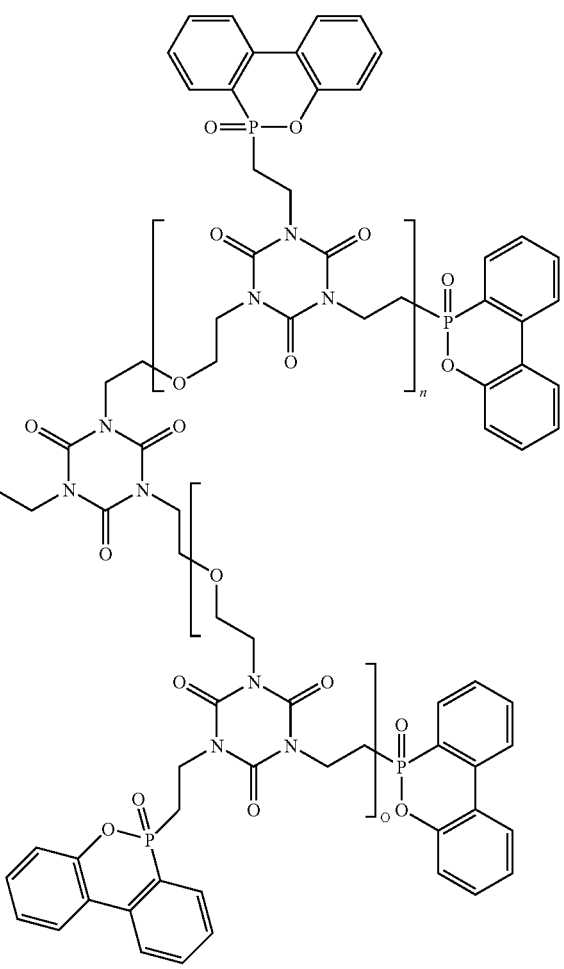

(II)

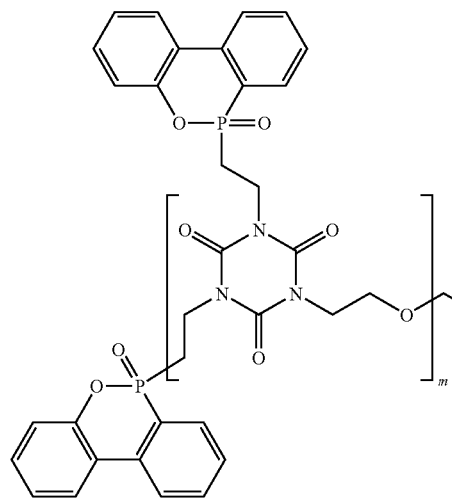

wherein R is one of the following radicals:

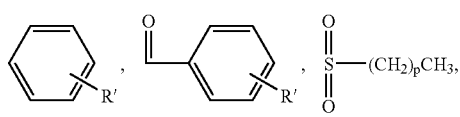

wherein l is an integer from 2 to 10, m and p are integers from 1 to 20, n and o are integers from 0 to 20 and R' is hydrogen or alkyl, in which (a) a 6-alkoxy-6H-dibenz[c,e][1,2]-oxaphosphorine is reacted with a bishydroxyalkyl amine or a polyvalent alcohol formed by polycondensation of 1,3,5-tris(2-hydroxyethyl)cyanuric acid while forming an intermediate product, and (b) said intermediate product obtained in step (a) is converted by adding a catalytic amount of an alkylating agent to a nitrous bridged 6H-dibenz[c,e][1,2]-oxaphosphorine-6-oxide derivative of Formula I or II.

Where in this application polyvalent molecular radicals are referred to, the bonding value of said molecular radicals is meant. Regarding alcohols, valence means the number of OH groups of the alcohol.

The use of polyvalent alcohols in the instant invention makes possible the production of polyvalent ("bridged") derivatives which during subsequent use as flameproofing agents in polymer networks can be more advantageously bonded in the polymers than non-bridged derivatives and can have an improved flameproofing effect.

For preparing the nitrous bridged 6H-dibenz[c,e][1,2]-oxaphosphorine-6-oxides of Formulae I and II, in a first step (a) a 6-alkoxy-6H-dibenz[c,e][1,2]-oxaphosphorine is reacted with a bishydroxyalkyl amine of Formula III or a polyvalent alcohol of Formula IV which previously was formed by polycondensation of 1,3,5-tris(2-hydroxyethyl)cyanuric acid, the bishydroxyalkyl amine and the polyvalent alcohol which have the formulae that follow, to form an intermediate product.

(III)

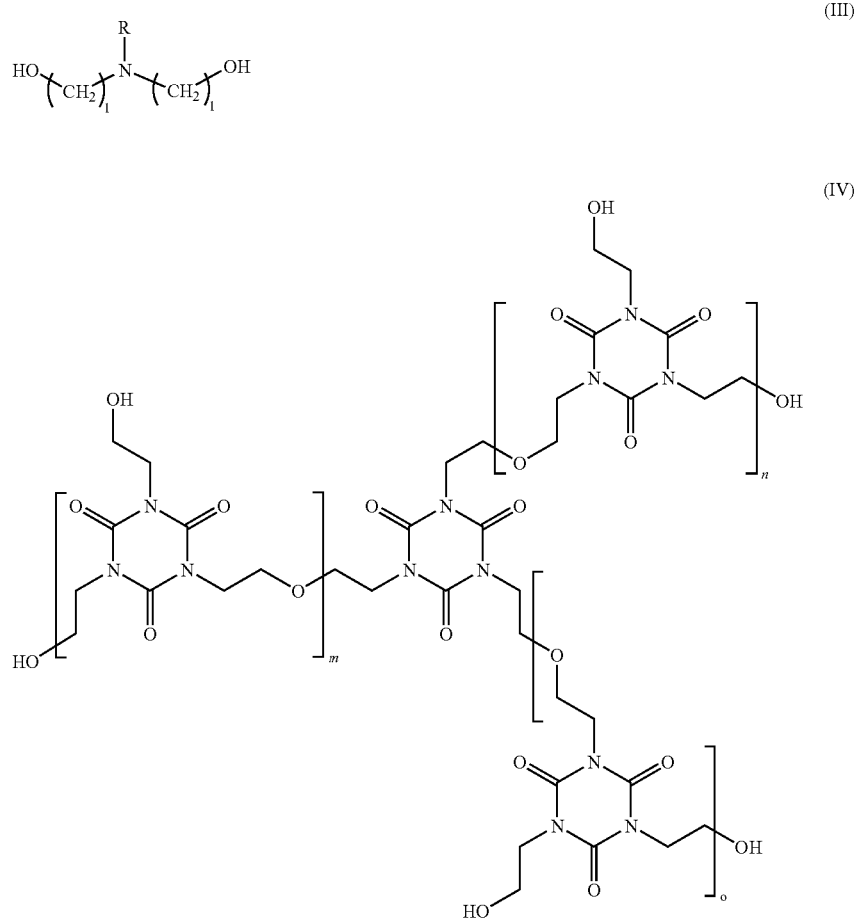

(IV)

As educt is used in step (a) of the process a 6-alkoxy-6H-dibenz[c,e][1,2]-oxaphosphorine prepared by the process disclosed in DE 102 06 982 A1. Starting from 6H-dibenz[c,e][1,2]-oxaphosphorine-6-oxide, 6-alkoxy-6H-dibenz[c,e][1,2]-oxaphosphorines are obtained by acid catalyzed reaction with orthocarbonic acid esters and suitable alcohols. Preferably used is 6-ethoxy 6H-dibenz[c,e][1,2]-oxaphosphorine as educt.

Suitable as bishydroxyalkyl amines are compounds of Formula III wherein R is one of the following radicals:

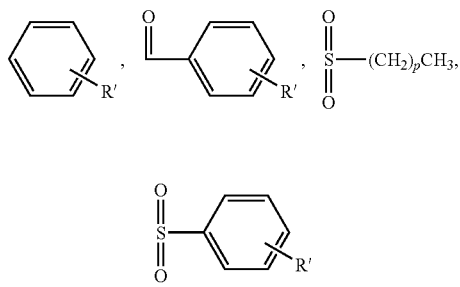

specially a phenyl or p-toluenesulfonyl group, where l is an integer from 2 to 10, and p is an integer from 1 to 20 and R' hydrogen or alkyl. Examples of suitable bishydroxyalkyl amines are bis(2-hydroxyethyl)p-toluenesulfonyl amine and bis(2-hydroxy ethyl)phenyl amine.

Suitable as polyvalent alcohols are compounds of the Formula IV wherein m is an integer from 1 to 20 and n and o are integers from 0 to 20. Particularly suitable are polyvalent alcohols of the Formula IVa derived from polyvalent alcohols of the Formula IV in which m is an integer from 1 to 20 and n and o=0.

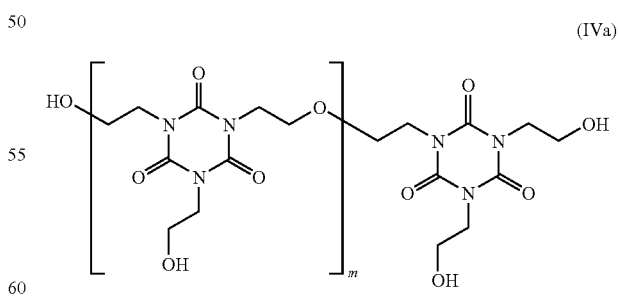

(IVa)

If alcohols of the Formula IVa are used in the process, there are obtained nitrous bridged derivatives of 6H-dibenz[c,e][1,2]-oxaphosphorine-6-oxides IIa which are derived from the derivatives of the Formula II in which m is an integer from 1 to 20 and n and o=0.

(IIa)

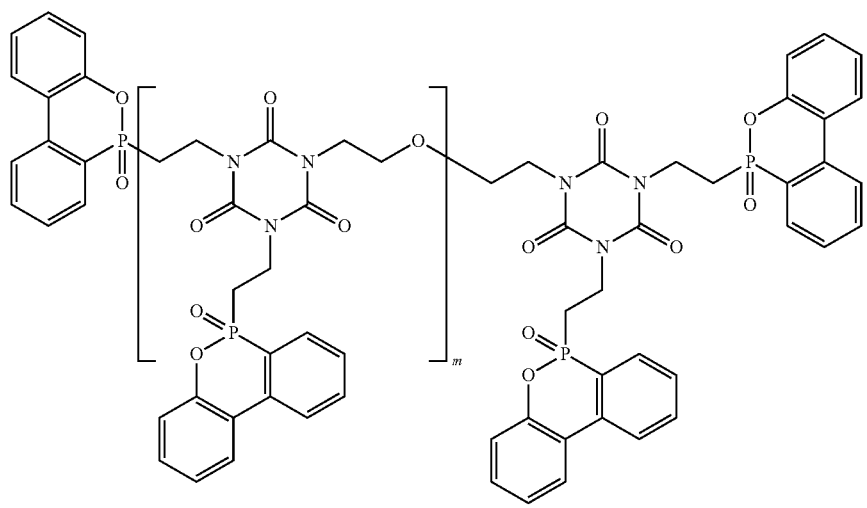

In a preferred embodiment the alcohol developing in step (a), which is ethanol if 6-ethoxy-6H-dibenz[c,e][1,2]-oxaphosphorine is used, is continuously removed from the reaction vessel. This has an advantage in that by removal of the alcohol the reaction balance is shifted to favor the intermediate product.

The intermediate product obtained in step (a) can be described by the following Formulae III' and IV' or IVa' (when a polyvalent alcohol of the Formula IVa is used)

(III')

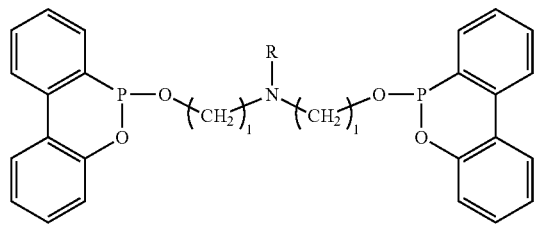

(IV')

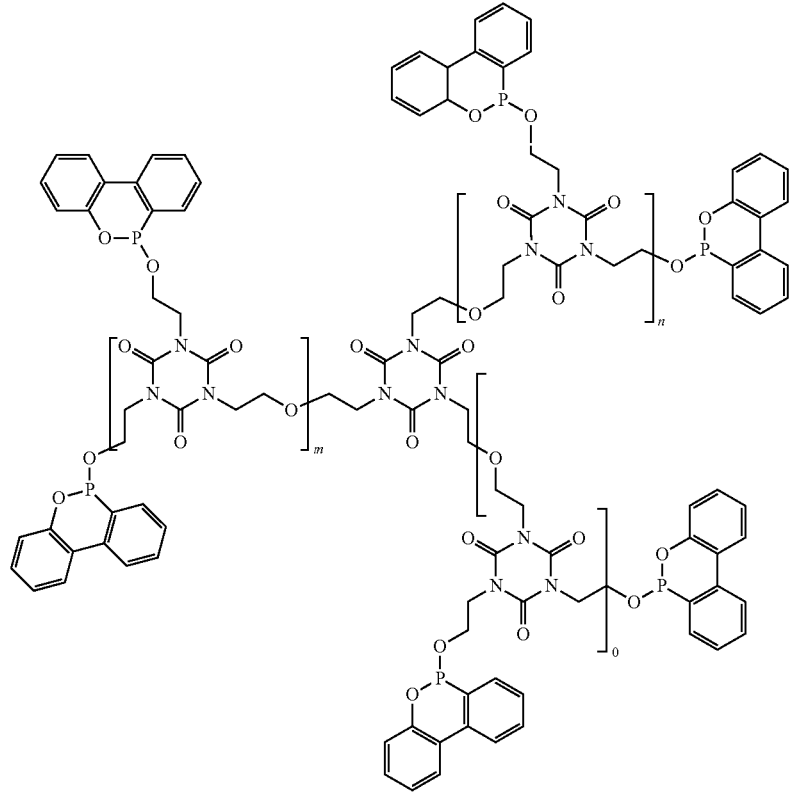

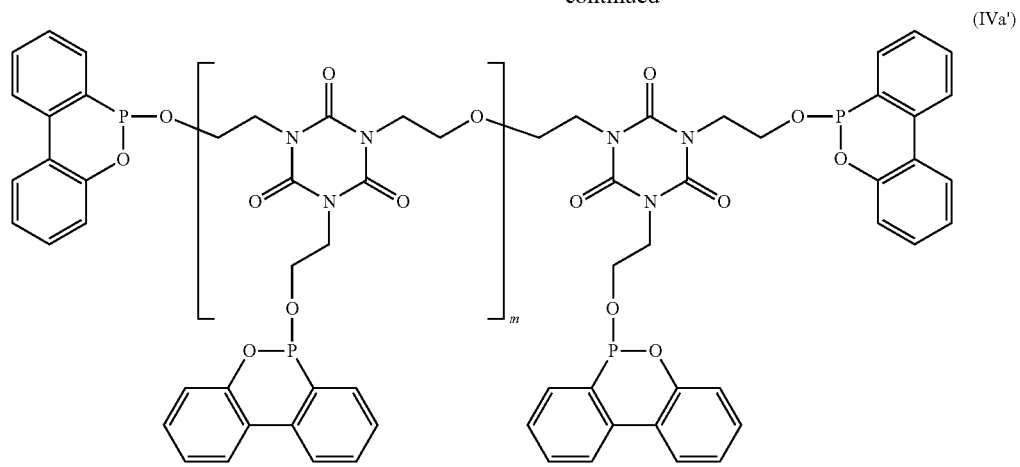

(IVa')

wherein the radicals R and R' and l, m, n, o and p, have the above given meanings.

In a preferred embodiment of the invention, after termination of the reaction in step (a), the 6-alkoxy-6H-dibenz[c,e][1,2]-oxaphosphorine in excess is distilled off under a medium-high vacuum in the range (0.01-0.001 mbar).

The intermediate products which are formed in the first step (a) are then, in a second step (b), converted by adding catalytic amounts of an alkylating agent to the nitrous bridged derivatives of 6H-dibenz[c,e][1,2]-oxaphosphorine-6-oxides of the Formulae I, II or IIa by means of an intramolecular Michaelis-Arbusov reaction. A halogen-free alkylating agent is added in catalytic amounts of preferably 1 to 10 mmole/mole in the presence of which a triple-bond intermediate product related to phosphorus is converted to a five-bond phosphorous compound. As alkylating agents can be used sulfuric acid esters and sulfonic acid esters. Preferred are sulfonic acid esters of aromatic sulfonic acids such as alkyl-p-toluene sulfonic acid ester, for example, p-toluene sulfonic acid methyl ester. Reaction (b) preferably is carried out at elevated temperatures of above 170° C. and under a protective gas such as argon or nitrogen.

Unlike a classic Michaelis-Arbusov reaction, the process of the present invention has the advantage that it is possible to eliminate halogen, since halogen-free alkylating agents such as sulfuric acid esters and sulfonic acid esters are used in catalytic amounts.

After the catalytic reaction in step (b) the product obtained is separated and optionally cleaned and dried.

Preferred compounds of the Formula I compounds are those in which R is an aryl group especially phenyl, or an aryl sulfonyl group especially p-toluenesulfonyl group and l is 2.

The process of the present invention has the particular advantage in that it can be carried out in a one-receptacle synthesis, that is, in a single reaction vessel with good yields without expensive cleaning operations between the reaction steps.

The nitrous bridged derivatives of 6H-dibenz[c,e][1,2]-oxaphosphorine-6-oxides of Formulae I or II and IIa are suitable as flameproofing agents for polymers, especially polyesters, polyamides, polycarbonates, polystyrenes, polyethylenes, polypropylenes, phenolic and epoxy resins.

The present invention also provides oligomers of the 1,3,5-tris(2-hydroxyethyl)cyanuric acid of the Formula IV

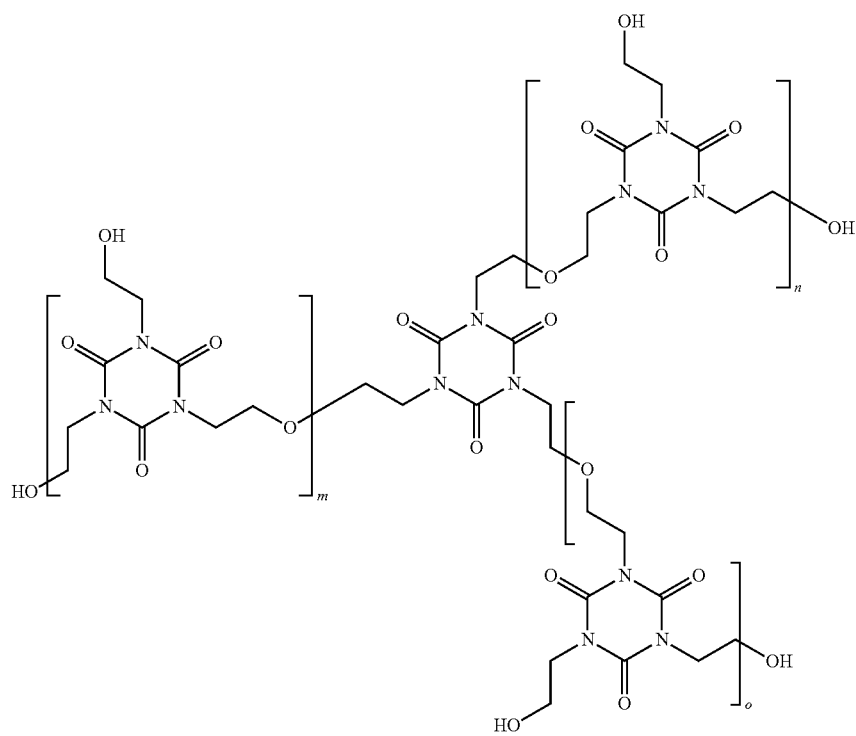

wherein m is an integer from 1 to 20 and n and o are integers from 0 to 20, and especially oligmers of the Formula IVa

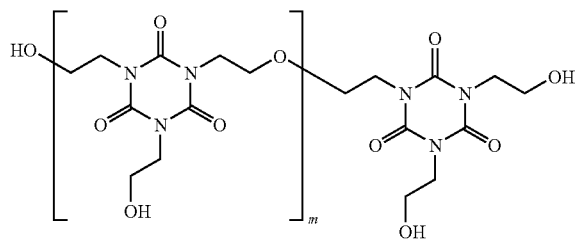

which derive from the oligomers of the Formula IV in which m is an integer from 1 to 20 and n and o=0.

The oligomers of Formula IV or IVa are reacted in step (a) together with the 6-alkoxy-6H-dibenz[c,e][1,2]-oxaphosphorine to prepare derivatives of Formula II or IIa.

The oligomers are prepared starting from 1,3,5-tris(2-hydroxyethyl)cyanuric acid which is subjected to an acid catalyzed polycondensation.

Preferred embodiments and advantages of the present invention are particularly shown in the examples.

EXAMPLE 1

Preparation of IVa

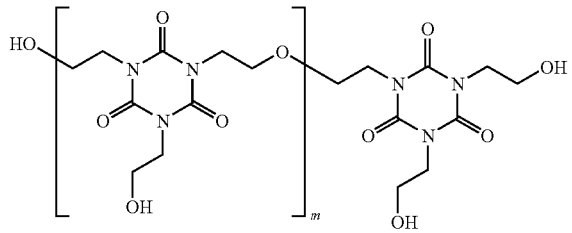

0.25 mole of 1,3,5-tris(2-hydroxyethyl)cyanuric acid and 7 g of a catalyst (p-toluene sulfonic acid bonded on a polymer carrier with about 0.003 mole $SO_3H$ groups per gram) are heated to 170° C. in a round-bottom flask equipped with an inner thermometer, a reflux cooler and an effective magnetic mixer. A light nitrogen flow is passed over the mixture which after melting of the 1,3,5-tris(2-hydroxyethyl)cyanuric acid is vigorously stirred. At 1 hour intervals the water generated is removed by brief application of vacuum. The reaction speed is at first low but gradually rises detectably to an increased separation of water droplets in the reflux cooler. After a reaction lasting from 10-15 hours at 170° C. the viscosity of the melt clearly increases. The reaction is interrupted when the melt even though semi-fluid still can be stirred (during further continuation of the condensation cross-linked insoluble products would be obtained). Prior to the cooling, vacuum is again applied (about mbar, for a few min). At about 80° C., 250 ml absolute dioxane are added and the mixture is heated under nitrogen until the solvent boils. It is kept boiling until complete solution of the product, and after cooling the product is filtered through a 10 mm thick layer of kieselguhr to entirely remove the catalyst. To the clear filtrate, 50 ml toluene was added and then the solvents, together with still contained water residues, are essentially completely removed at about 50 mbar, being gradually heated up to about 110° C. The still hot residue is then again solved in 130 ml absolute dioxane and a few drops of triethanole amine and 3 g orthoformic acid ethyl ester are added so as to remove any remaining acid or water traces. By concentrating to about half of the starting volume at 50 mbar, a concentrated solution is obtained of the oligomerized 1,3,5-tris(2-hydroxyethyl)cyanuric acid.

EXAMPLE 2

Preparation of Ia, (R=p-toluenesulfonyl, l=2)

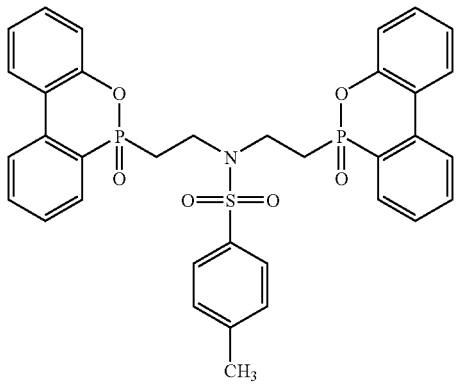

A mixture of 20.75 g (0.080 mole) N,N-bis(2-hydroxyethyl)-p-toluene sulfonamide and 44.96 g (0.184 mole) 6-ethoxy-6H-dibenz[c,e][[1,2]-oxaphosphorine is stirred under a vacuum (about 10 mbar) for 18 hours at 120° C. Excess 6-ethoxy-6H-dibenz[c,e][1,2]-oxaphosphorine is then distilled off under a vacuum of 0.001 mbar. The distillation residue is heated under argon to 180° C. after adding 1.3 g (0.007 mole)-p-toluene sulfonic acid methyl ester. This temperature is maintained for 24 hours. After cooling, the product is dissolved in methylene chloride. Diethyl ether is then added, and the raw product precipitated. The raw product is then filtered off and dissolved in hot methanol. On cooling of the methanolic solution, the product separates in finely crystalline form. The product is then filtered off and dried under vacuum at about 80° C. The yield amounts to 14.1 g (30%) Ia.

EXAMPLE 3

Preparation of Ib, (R=phenyl, l=2)

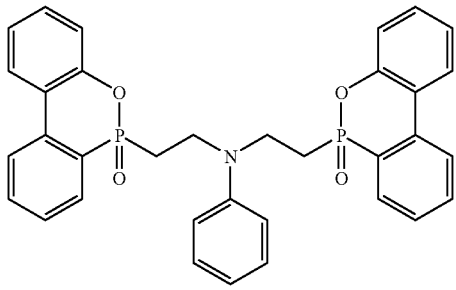

A mixture of 10.98 g (0.045 mole) 6-ethoxy-6H-dibenz[c,e][1,2]-oxaphosphorine and 2.85 g (0.0157 mole) N-phenyl diethanolamine is stirred for 18 hours at 120° C. under a vacuum (about 10 mbar). Excess 6-ethoxy-6H-dibenz[c,e][1,2]-oxaphosphorine is distilled off under a medium-high vacuum (0.001 mbar). After adding 0.3 g (0.0016 mole)p-toluene sulfonic acid methyl ester, the distillation residue is heated to 190° C. under argon and held for 19 hours at this temperature. After cooling the substance is dissolved in methylene chloride. The raw product is precipitated by adding diethyl ether. The diethyl ether is pulled off and the product is then dissolved in methanol. The methanolic solution is slowly cooled down to about −30° C. The methanol is then pulled off, and the product heated to 70° C. in vacuum (yield 4.98 g or 55%).

EXAMPLE 4

Preparation of IIa

A compound of Formula IVa solution in dioxane is heated under nitrogen to about 100° C. and 139 g (0.57 mole) of likewise heated 6-ethoxy-6H-dibenz[c,e][1,2]-oxaphosphorine is added with vigorous stirring. The dioxane is then removed at about 50 mbar, the mixture being gradually heated to 135° C. The pressure is then lowered to 1 mbar and the mixture is vigorously stirred. The temperature is gradually raised over the course of 10 hours from 135° C. to 160° C. The mixture is then stirred for 2 more hours at 160° C. and 1 mbar. Ethanol product is distilled off under vacuum and is collected in a low-temperature trap. The initially two-phase mixture gradually becomes homogeneous and its viscosity clearly increases. After terminating the reaction, the excess ethoxy-6H-dibenz[c,e][1,2]-oxaphosphorine is distilled off under medium-high vacuum (0.001 mbar), while being heated to a maximum of 175° C. After adding 0.74 g (0.004 mole) p-toluene sulfonic acid methyl ester, the distillation residue becomes thickly viscous when heated under nitrogen for 15 hours at 175° C., but after heating to about 220° C. it can be poured from the flask. After cooling to room temperature the product can be easily pulverized and has a medium mole mass of $M_n$=2000-5000 g/mole (depending on the oligomerization degree of the starting material).

The invention claimed is:

1. A process for preparation of nitrous bridged derivatives of 6H-dibenz[c,e][1,2]-oxaphosphorine-6-oxides of Formulae (I) and (II)

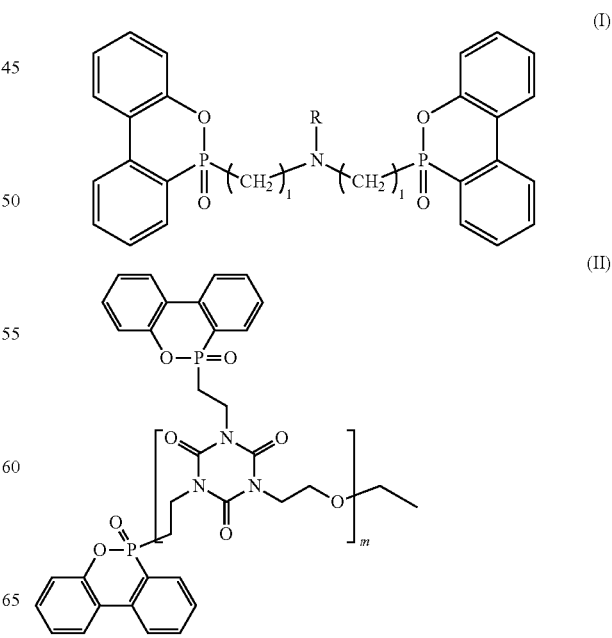

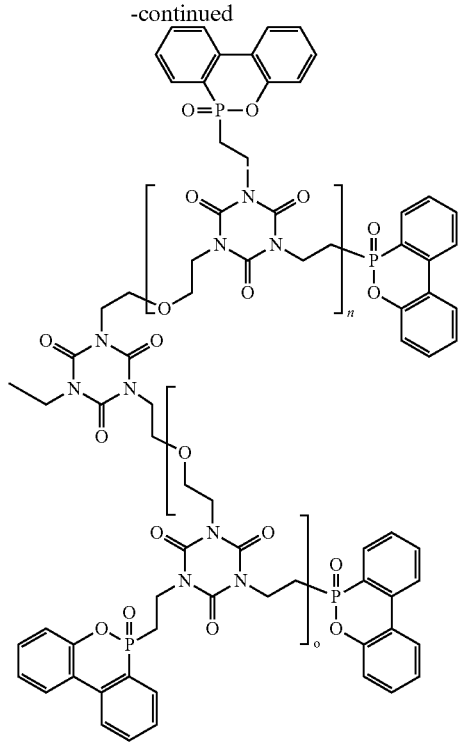

wherein R is one of the following radicals:

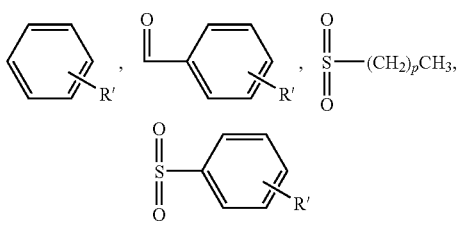

wherein l is an integer of from 2 to 10, m and p are integers of from 1 to 20, n and o are each 0 or are integers from 1 to 20 and R' is hydrogen or an alkyl group wherein:
(a) a 6-alkoxy-6H-dibenz[c,e][1,2]-oxaphosphorine is reacted with a bishydroxyalkyl amine or a polyvalent alcohol formed by polycondensation of 1,3,5-tris(2-hydroxyethyl)cyanuric acid, to form an intermediate product and
(b) said intermediate product obtained in step (a) is converted by adding a catalytic amount of an alkylating agent to a nitrous bridged 6H-dibenz[c,e][1,2]-oxaphosphorine-6-oxide derivative of the Formula (I) or (II).

2. The process according to claim 1, wherein in step (a), the bishydroxyalyl amine is a bishydroxyalkylamine of formula (III) or the polyvalent alcohol is a polyvalent alcohol of formula (IV) bishydroxyalkyl amine of the Formula (III) or a polyvalent alcohol of the Formula (IV)

(III)

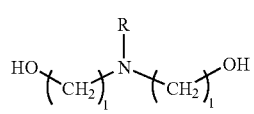

(IV)

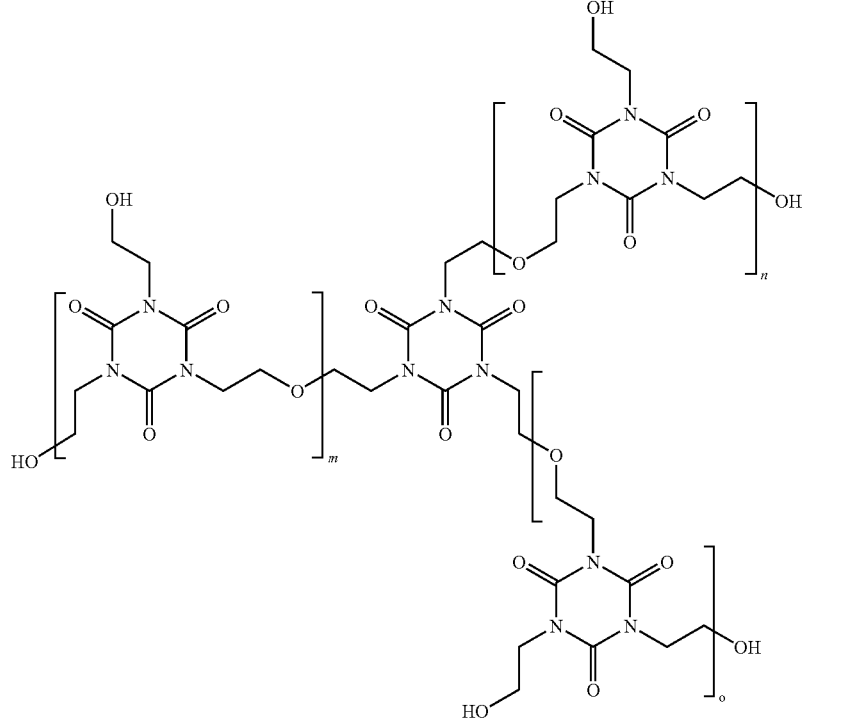

wherein R is one of the following radicals:

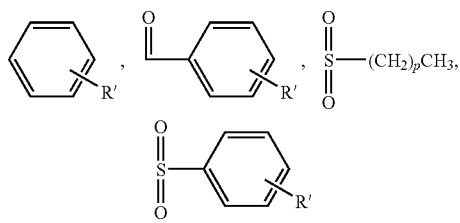

wherein l is an integer from 2 to 10, m and p are integers from 1 to 20, n and o are each 0 or integers from 1 to 20, and R' is hydrogen or an alkyl group.

3. The process according to claim 1, wherein there is produced nitrous bridged derivatives of 6H-dibenz[c,e][1,2]-oxaphosphorine-6-oxides of the Formula (IIa)

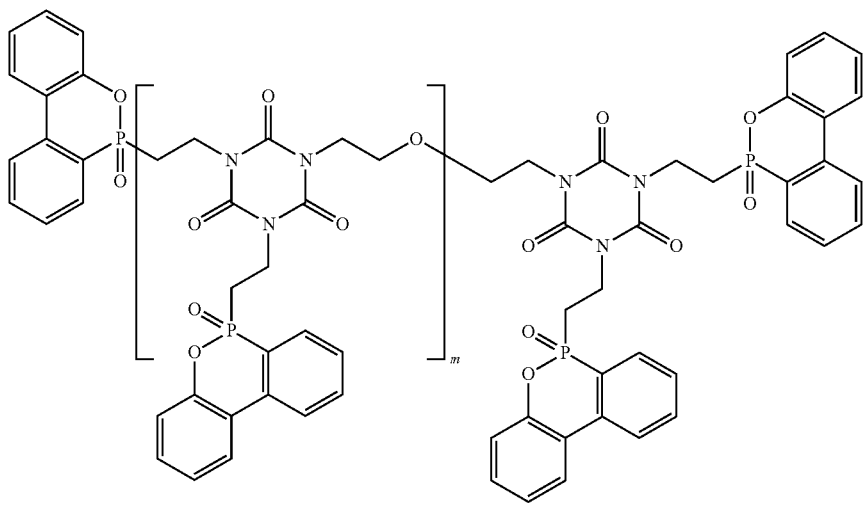

which derive from nitrous bridged derivatives of 6H-dibenz[c,e][1,2]-oxaphosphorine-6-oxides of the Formula (II) in which m is an integer of from 1 to 20, and n and o are 0.

4. The process according to claim 2, wherein in step (a) the polyvalent alcohol is polyvalent alcohol of the Formula (IVa)

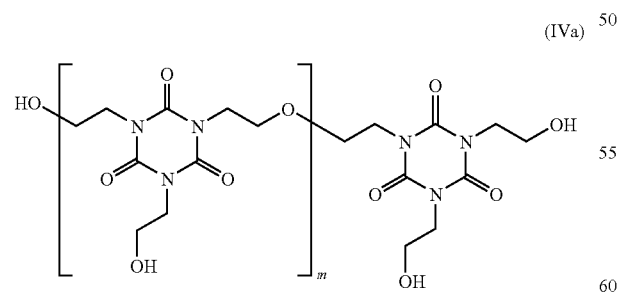

derived from the polyvalent alcohol of the Formula (IV) in which m is an integer from 1 to 20 and n and o are 0.

5. The process according to claim 2, wherein in the bishydroxyalkyl amine R is a phenyl or p-toluenesulfonyl group is used in step (a).

6. The process according to claim 2, wherein bis(hydroxyethyl) phenyl amine or bis(hydroxyethyl)p-toluenesulfonylamine is the bishydroxyalkyl amine in step (a).

7. The process according to claim 5, wherein bis(hydroxyethyl) phenyl amine or bis(hydroxyethyl)p-toluenesulfonylamine is the bishydroxyalkyl amine in step (a).

8. The process according to claim 1, wherein 6-ethoxy-6H-dibenz[c,e][1,2]-oxaphosphorine is the 6-alkoxy-6H-dibenz[c,e][1,2]- oxaphosphorine step (a).

9. The process according to claim 1, wherein the alkylating agent in step (b) is selected from the group consisting of a sulfuric acid ester and a sulfonic acid ester.

10. The process according to claim 9, wherein the alkylating agent in step (b) is p-toluene sulfonic acid methyl ester.

11. The process according to claim 1, wherein alcohol formed as a by-product in step (a) is removed.

12. The process according to claim 1, wherein steps (a) and (b) are carried out in a single reaction vessel.

13. The process according to claim 1, wherein process is conducted in a reaction vessel equipped with a reflux cooler and stirrer, and the following steps are subsequently carried out while constantly stirring:
(a) 6-ethoxy-6H-dibenz[c,e][1,2]-oxaphosphorine and the bishydroxyalkyl amine or the polyvalent alcohol are mixed at room temperature in the reaction vessel;
(b) the mixture obtained in step (a) is heated while simultaneously distilling off ethanol generated;
(c) the p-toluene sulfonic acid methyl ester is added to the distillation residue of step (b), and the mixture obtained is heated
after which the compound of Formula (I) or (II) is separated.

14. The process according to claim 13, further including the step of cleaning and drying the compound resulting from step (c).

15. The process according to claim 13, wherein subsequent to step (b) excess 6-ethoxy-6H-dibenz[c,e][1,2]-oxaphosphorine is distilled off under high-medium vacuum (0.01-0.001 mbar).

16. Nitrous bridged derivatives of 6H-dibenz[c,e][1,2]-oxaphosphorine-6-oxides of the Formulae (I) and (II)

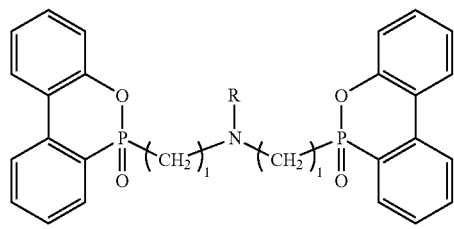
(I)

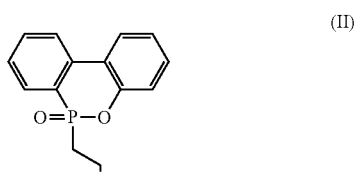
(II)

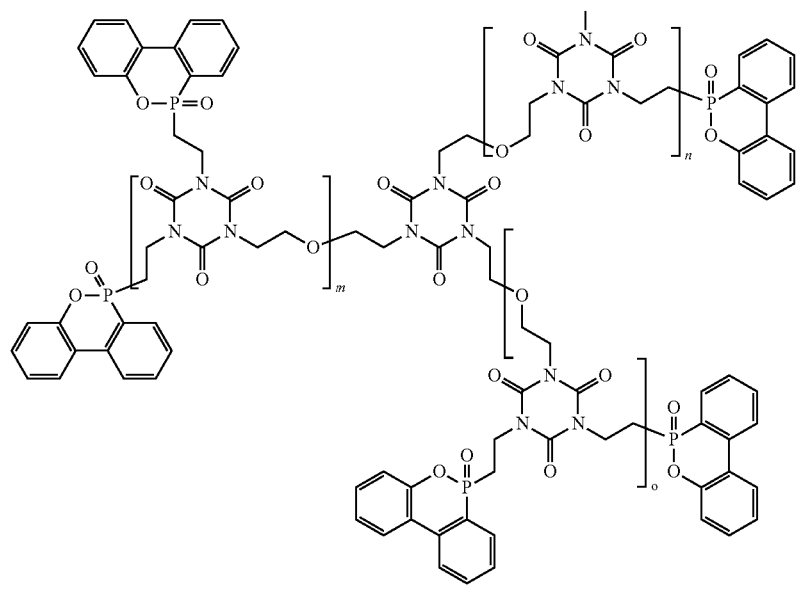

wherein R is one of the following radicals:

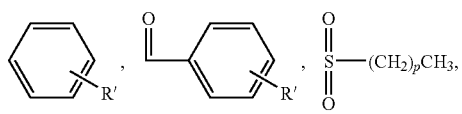

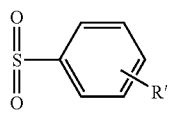

l an integer from 2 to 10, m and p are integers from 1 to 20, n and o are each 0 or integers from 1 to 20 and R' is hydrogen or alkyl.

17. A nitrous bridged derivative of 6H-dibenz[c,e][1,2]-oxaphosphorine-6-oxides according to claim 16, wherein R is a phenyl or a p-toluenesulfonyl group.

18. A nitrous bridged derivative of 6H-dibenz[c,e][1,2]-oxaphosphorine-6-oxides according to claim 16, wherein R is a phenyl or a p-toluenesulfonyl group and l equals 2.

19. A nitrous bridged derivative of 6H-dibenz[c,e][1,2]-oxaphosphorine-6-oxides according to claim 16, having a structure of the Formula (IIa)

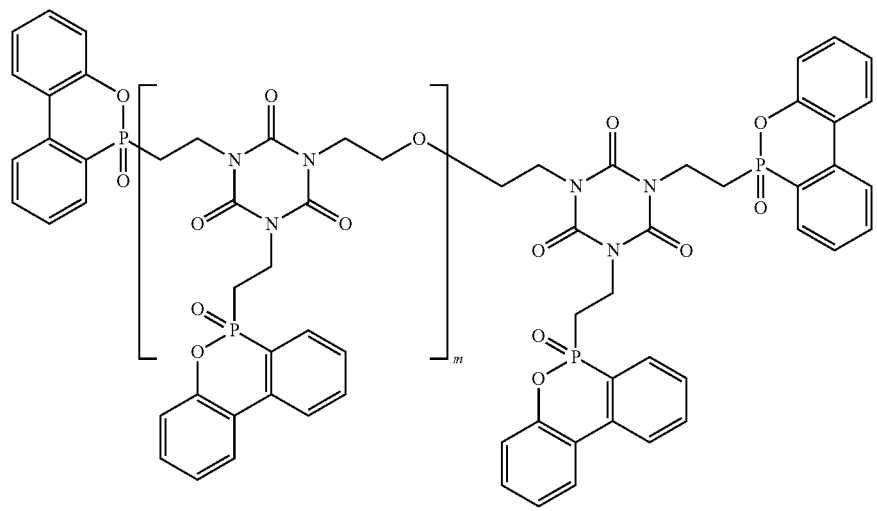

(IIa)

derived from Formula (II) in which m is an integer of from 1 to 20 and n and o are 0.

20. A process for flameproofing polymers and products prepared therefrom, which comprises adding to the polymers a 6H-dibenz[c,e][1,2]-oxaphosphorine-6-oxide derivative prepared by a process according to claim 1.

21. The process of claim 19, wherein the polymer is selected from the group consisting of a polyester, a polyamide, a polycarbonate, a polystyrene, polyethylene, polypropylene, phenolic resin and an epoxy resin.

22. An oligomer of the 1,3,5-tris(2-hydroxyethyl)cyanuric acid of the Formula (IV)

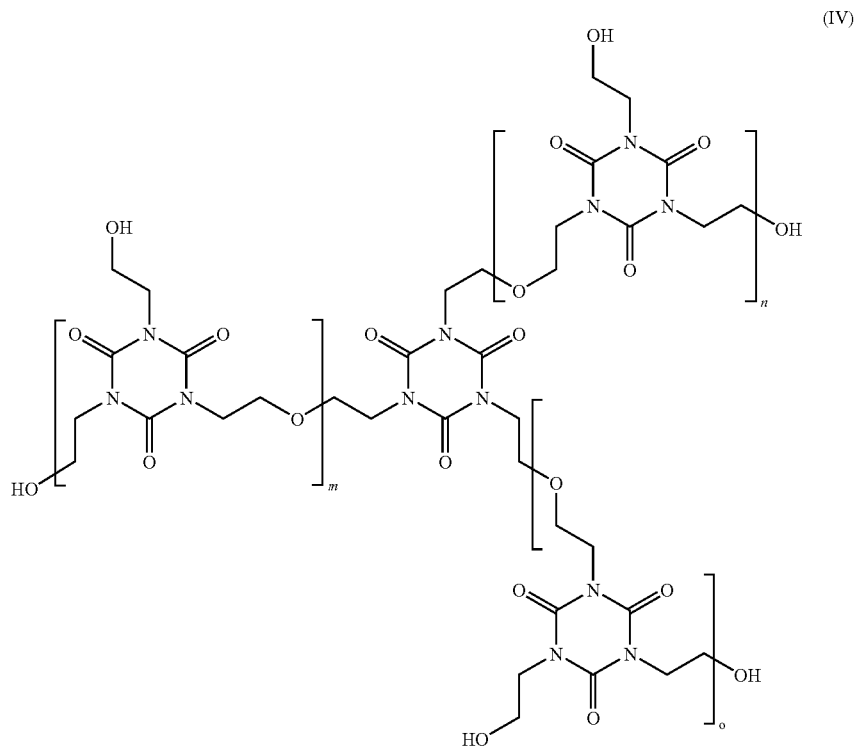

(IV)

wherein m is an integer from 1 to 20 and n and o are 0 or integers from 1 to 20.
23. The oligomer according to claim 22, having the Formula (IVa)
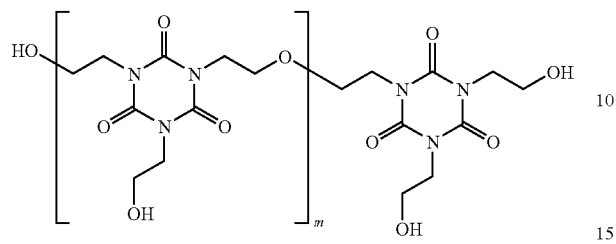
(IVa)
the structure of which derives from Formula (IV) in which m is an integer from 1 to 20 and n and o and 0.
\* \* \* \* \*